(12) United States Patent
Cox et al.

(10) Patent No.: US 8,017,624 B2
(45) Date of Patent: *Sep. 13, 2011

(54) FUSED AMINOPIPERIDINES AS DIPEPTIDYI PEPTIDASE-IV INHIBITORS FOR THE TREATMENT OR PREVENTION OF DIABETES

(75) Inventors: Jason M. Cox, East Windsor, NJ (US); Scott D. Edmondson, Clark, NJ (US); Anthony Mastracchio, Pasadena, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 864 days.

This patent is subject to a terminal disclaimer.

(21) Appl. No.: 11/990,037

(22) PCT Filed: Aug. 22, 2006

(86) PCT No.: PCT/US2006/032989
§ 371 (c)(1),
(2), (4) Date: Feb. 5, 2008

(87) PCT Pub. No.: WO2007/024993
PCT Pub. Date: Mar. 1, 2007

(65) Prior Publication Data
US 2009/0258894 A1    Oct. 15, 2009

Related U.S. Application Data

(60) Provisional application No. 60/711,756, filed on Aug. 26, 2005.

(51) Int. Cl.
*A61K 31/437* (2006.01)
*C07D 487/04* (2006.01)

(52) U.S. Cl. .......................................... 514/290; 546/82
(58) Field of Classification Search .................... 546/82; 514/290
See application file for complete search history.

(56) References Cited

U.S. PATENT DOCUMENTS

| | | |
|---|---|---|
| 2004/0242568 A1 | 12/2004 | Feng et al. |
| 2005/0070535 A1 | 3/2005 | Feng et al. |
| 2005/0131019 A1 | 6/2005 | Pei et al. |
| 2007/0208010 A1 | 9/2007 | Weber et al. |
| 2007/0254865 A1 | 11/2007 | Biftu et al. |
| 2008/0009510 A1 | 1/2008 | Edmondson et al. |
| 2008/0076773 A1 | 3/2008 | Cox et al. |
| 2009/0233936 A1 | 9/2009 | Cox et al. |

FOREIGN PATENT DOCUMENTS

| | | |
|---|---|---|
| WO | WO 2006/009886 A1 | 1/2006 |
| WO | WO 2006/023750 A2 | 3/2006 |
| WO | WO 2006/023750 A3 | 3/2006 |
| WO | WO 2006/039325 A2 | 4/2006 |
| WO | WO 2006/039325 A3 | 4/2006 |
| WO | WO 2006/058064 A2 | 6/2006 |
| WO | WO 2006/058064 A3 | 6/2006 |
| WO | WO 2006/127530 A2 | 11/2006 |
| WO | WO 2007/070434 A2 | 6/2007 |
| WO | WO 2007/070434 A3 | 6/2007 |
| WO | WO 2007/087231 A2 | 8/2007 |
| WO | WO 2007/087231 A3 | 8/2007 |

OTHER PUBLICATIONS

Dorwald F. A. Side Reactions in Organic Synthesis, 2005, Wiley: VCH, Weinheim p. IX of Preface.*

* cited by examiner

*Primary Examiner* — Rita Desai
(74) *Attorney, Agent, or Firm* — Janet E. Fair; John C. Todaro

(57) ABSTRACT

The present invention is directed to novel substituted fused aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

17 Claims, No Drawings

FUSED AMINOPIPERIDINES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US06/032989, filed 22 Aug. 2006, which claims the benefit under 35 U.S.C. 119(e) of U.S. Provisional Application No. 60/711,756 filed 26 Aug. 2005.

FIELD OF THE INVENTION

The present invention relates to novel substituted fused aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV") enzyme are also under investigation as drugs that may be useful in the treatment of diabetes, and particularly Type 2 diabetes. See for example WO 97/40832, WO 98/19998, U.S. Pat. No. 5,939,560, Bioorg. Med. Chem. Lett., 6: 1163-1166 (1996); and Bioorg. Med. Chem. Lett., 6: 2745-2748 (1996). The usefulness of DPP-IV inhibitors in the treatment of Type 2 diabetes is based on the fact that DPP-UV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively to date, especially for utilities other than diabetes. New compounds are needed so that improved DPP-IV inhibitors can be found for the treatment of diabetes and potentially other diseases and conditions. The therapeutic potential of DPP-IV inhibitors for the treatment of Type 2 diabetes is discussed by D. J. Drucker in *Exp. Opin. Invest. Drugs,* 12: 87-100 (2003) and by K. Augustyns, et al., in *Exp. Opin. Ther. Patents,* 13: 499-510 (2003).

SUMMARY OF THE INVENTION

The present invention is directed to novel substituted fused aminopiperidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to substituted fused aminopiperidines useful as inhibitors of dipeptidyl peptidase-IV. Compounds of the present invention are described by structural formula I:

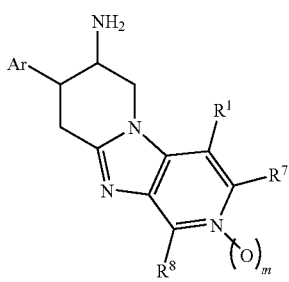

(I)

or a pharmaceutically acceptable salt thereof; wherein
m is 0 or 1;
each n is independently 0, 1, or 2;
Ar is phenyl unsubstituted or substituted with one to five $R^2$ substituents;
each $R^2$ is independently selected from the group consisting of fluorine, chlorine, methyl, and trifluoromethyl;
$R^1$, $R^7$ and $R^8$ are each independently selected from the group consisting of
 hydrogen,
 hydroxy,
 halogen,
 cyano,
 nitro,
 $C_{1-10}$ alkoxy, wherein alkoxy is unsubstituted or substituted with one to five substituents independently selected from halogen or hydroxy,
 $C_{1-10}$ alkyl, wherein alkyl is unsubstituted or substituted with one to five substituents independently selected from halogen or hydroxy,
 $C_{1-10}$ alkenyl, unsubstituted or substituted with one to five substituents independently selected from halogen or hydroxy,
 $(CH_2)_n$-aryl, wherein aryl is unsubstituted or substituted with one to five substituents independently selected hydroxy, halogen, cyano, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
 $(CH_2)_n$-heteroaryl, wherein heteroaryl is unsubstituted or substituted with one to three substituents independently selected from hydroxy, halogen, cyano, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
 $(CH_2)_n$-heterocyclyl, wherein heterocyclyl is unsubstituted or substituted with one to three substituents independently selected from oxo, hydroxy, halogen, cyano, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
 $(CH_2)_n$—$C_{3-6}$ cycloalkyl, wherein cycloalkyl is unsubstituted or substituted with one to three substituents independently selected from halogen, hydroxy, cyano, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
 $(CH_2)_n$—COOH,
 $(CH_2)_n$—COO$C_{1-6}$ alkyl,
 $(CH_2)_n$—NR$^3$R$^4$,
 $(CH_2)_n$—CONR$^3$R$^4$,
 $(CH_2)_n$—OCONR$^3$R$^4$,
 $(CH_2)_n$—SO$_2$NR$^3$R$^4$,
 $(CH_2)_n$—SO$_2$R$^5$,
 $(CH_2)_n$—SOR$^5$,
 $(CH_2)_n$—SR$^6$,
 $(CH_2)_n$—NR$^6$SO$_2$R$^5$,
 $(CH_2)_n$—NR$^6$CONR$^3$R$^4$,
 $(CH_2)_n$—NR$^6$COR$^6$, and
 $(CH_2)_n$—NR$^6$CO$_2$R$^5$;
wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
$R^3$ and $R^4$ are each independently selected from the group consisting of
 hydrogen,
 $(CH_2)_n$-phenyl,
 $(CH_2)_n$—$C_{3-6}$ cycloalkyl, and
 $C_{1-6}$ alkyl,
wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to four substituents independently selected from halogen, hydroxy, $C_{1-6}$ alkyl, and $C_{1-6}$ alkoxy, wherein alkyl and alkoxy are unsubstituted or substituted with one to five halogens;

each $R^5$ is independently $C_{1-6}$ alkyl, wherein alkyl is unsubstituted or substituted with one to five substituents independently selected from halogen and hydroxy; and $R^6$ is hydrogen or $R^5$.

In one embodiment of the compounds of the present invention, m is 0.

In a second embodiment of the compounds of the present invention, m is 1.

In a third embodiment of the compounds of the present invention, Ar is 2,4,5-trifluorophenyl or 2,5-difluorophenyl.

In a fourth embodiment of the compounds of the present invention, $R^1$, $R^7$ and $R^8$ are each independently selected from the group consisting of hydrogen, halogen, $C_{1-4}$ alkoxy, wherein alkoxy is unsubstituted or substituted with one to five fluorines, $C_{1-4}$ alkyl, wherein alkyl is unsubstituted or substituted with one to five fluorines, $C_{1-4}$ alkenyl, unsubstituted or substituted with one to five fluorines, and $C_{3-6}$ cycloallyl.

In a class of this fourth embodiment, $R^1$ is hydrogen.

In a fifth embodiment of the compounds of the present invention, there are provided compounds of structural formulae Ia and Ib of the indicated stereochemical configuration having a trans orientation of the Ar and $NH_2$ substituents on the two stereogenic carbon atoms marked with an *:

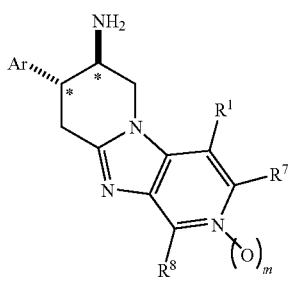

(Ia)

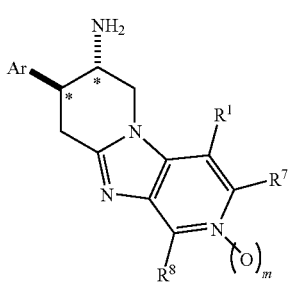

(Ib)

wherein m, Ar, $R^1$, $R^7$ and $R^8$ are as described above.

In a class of this fifth embodiment, there are provided compounds of structural formula Ia of the indicated absolute stereochemical configuration having a trans orientation of the Ar and $NH_2$ substituents on the two stereogenic carbon atoms marked with an *:

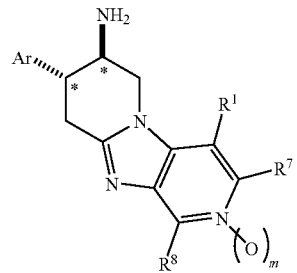

(Ia)

wherein m, Ar, $R^1$, $R^7$ and $R^8$ are as described above.

In a subclass of this class, m is 0; $R^1$ is hydrogen; Ar is 2,4,5-trifluorophenyl or difluorophenyl; and $R^7$ and $R^8$ are each independently selected from the group consisting of hydrogen, halogen, $C_{1-4}$ alkoxy, wherein alkoxy is unsubstituted or substituted with one to five fluorines, $C_{1-4}$ alkyl, wherein alkyl is unsubstituted or substituted with one to five fluorines, $C_{1-4}$ alkenyl, unsubstituted or substituted with one to five fluorines, and $C_{3-6}$ cycloalkyl.

In another subclass of this class, m is 1; $R^1$ is hydrogen; Ar is 2,4,5-trifluorophenyl or difluorophenyl; and $R^7$ and $R^8$ are each independently selected from the group consisting of hydrogen, halogen, $C_{1-4}$ alkoxy, wherein alkoxy is unsubstituted or substituted with one to five fluorines, $C_{1-4}$ alkyl, wherein alkyl is unsubstituted or substituted with one to five fluorines, $C_{1-4}$ alkenyl, unsubstituted or substituted with one to five fluorines, and $C_{3-6}$ cycloallyl.

Nonlimiting examples of compounds of the present invention that are useful as dipeptidyl peptidase-IV inhibitors are the following structures having the indicated absolute stereochemical configurations at the two stereogenic fused piperidine carbon atoms:

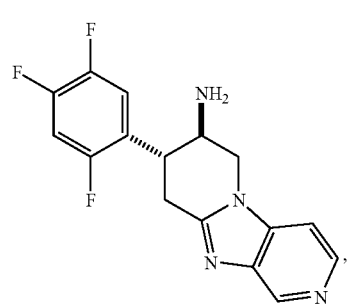

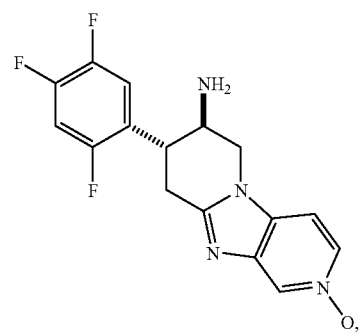

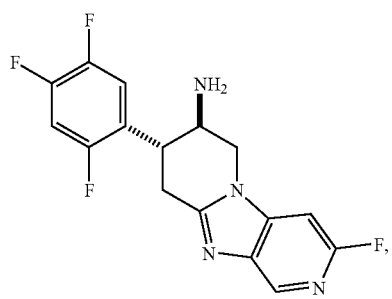

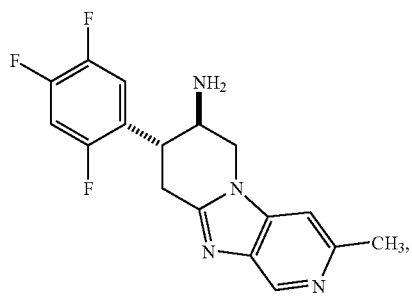

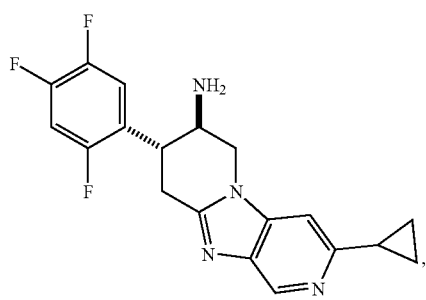

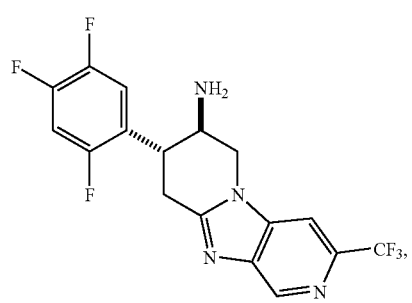

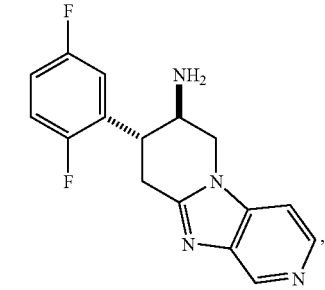

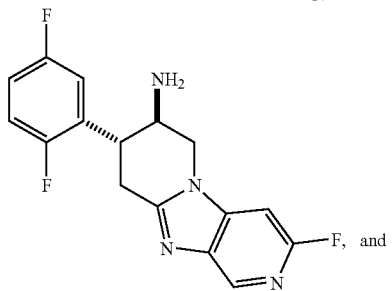

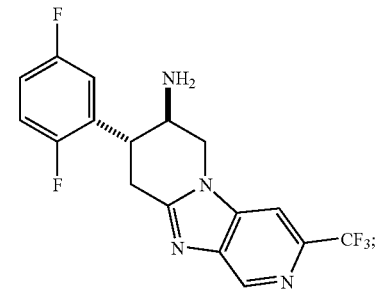

and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term allyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$-alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atoms marked with an * in formulae Ia and Ib. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formulae Ia and Ib show the preferred stereochemistry at the stereogenic carbon atoms to which are attached the $NH_2$ and Ar groups on the cyclohexane ring.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m=50$ µM; $k_{cat}=75$ s$^{-1}$; $k_{cat}/K_m=1.5\times10^6$ M$^{-1}$s$^{-1}$. A typical reaction contains approximately 50 µM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an IC$_{50}$ of less than about 1 μM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis. The DPP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine* 6: 802-807 (2000)). In addition, studies with DPP-IV deficient mice suggest that these animals are resistant to diet-induced obesity and associated pathology (e.g. hyperinsulinonemia).

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DPP-IV inhibitor diprotin A; and (3) GRF[3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-UV, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-UV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation* 63: 1495-1500 (1997)). DPP-IV inhibitors have been tested in collagen and allyldiamine-induced arthritis in rats and showed a statistically significant attenuation of hind paw swelling in this model [*Int. J. Immunopharmacology* 19:15-24 (1997) and *Immunopharmacology*, 40: 21-26 (1998)]. DPP-IV is upregulated in a number of autoimmune diseases including rheumatoid arthritis, multiple sclerosis, Graves' disease, and Hashimoto's thyroiditis (*Immunology Today* 20: 367-375 (1999)).

HIV Infection: DPP-IV inhibition may be useful for the treatment or prevention of HIV infection or AIDS because a number of chemolcines which inhibit HIV cell entry are potential substrates for DPP-IV (*Immunology Today* 20: 367-375 (1999)). In the case of SDF-1alpha, cleavage decreases antiviral activity (PNAS, 95: 6331-6 (1998)). Thus, stabilization of SDF-1 alpha through inhibition of DPP-IV would be expected to decrease HIV infectivity.

Hematopoiesis: DPP-IV inhibition may be useful for the treatment or prevention of hematopiesis because DPP-IV may be involved in hematopoiesis. A DPP-UV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-UV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6 M^{-1}s^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminogeptidases: Basic Science and Clinical Applications*, Sep. 26-29, 2002 (Berlin, Germany)].

Anxiety: Rats naturally deficient in DPP-IV have an anxiolytic phenotype (WO 02/34243; Karl et al., *Physiol. Behav.* 2003). DPP-IV deficient mice also have an anxiolytic phenotype using the porsolt and light/dark models. Thus DPP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-IV inhibitors are expected to show similar effects Myocardial Infarction: GLP-1 has been shown to be beneficial when administered to patients following acute myocardial infarction (Circulation, 109: 962-965 (2004)). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.*, 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (Eur. J. Clin. Chem. Clin. Biochem., 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.*, 37: 167-173 (1992)).

Osteoporosis: DPP-IV inhibition may be useful for the treatment or prevention of osteoporosis because GIP receptors are present in osteoblasts.

Stem Cell Transplantation: Inhibition of DPP-IV on donor stem cells has been shown to lead to an enhancement of their bone marrow homing efficiency and engraftment, and an increase in survival in mice (Christopherson, et al., *Science*, 305:1000-1003 (2004)). Thus DPP-IV inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, (35) anxiety, (36) memory deficit, (37) cognition deficit, (38) stroke, (39) Alzheimer's disease, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoallyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, bombesin receptor agonists (such as bombesin receptor subtype-3 agonists), cholecystolinin 1 (CCK-1) receptor agonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidide (P32/98); NVP-DPP-728; vildagliptin (LAF 237); P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB 1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chali et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1

Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 05/000809; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. Nos. 6,294,534, 6,350,760, 6,376,509, 6,410,548, 6,458,790, 6,472,398, 5,837,521, 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

The potential utility of safe and effective activators of glucokinase (GKAs) for the treatment of diabetes is discussed in J. Grimsby et al., "Allosteric Activators of Glucokinase: Potential Role in Diabetes Therapy," *Science,* 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos.

4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared from intermediates such as those of formula II and a haloaminopyridine such as III using standard coupling conditions followed by condensation and deprotection. The preparation of these intermediates is described in the following Schemes, wherein Ar, $R^1$, $R^7$ and $R^8$ are as defined above and P is a suitable nitrogen protecting group such as tert-butoxycarbonyl (Boc), benzyloxycarbonyl (Cbz), and 9-fluorenylmethoxycarbonyl (Fmoc).

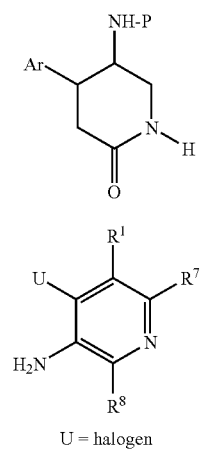

U = halogen

Compounds of formula IIa, wherein P is Boc, may be prepared from intermediate 6 using a route described in Scheme 1. Intermediates of formula 6 are known in the literature or may be conveniently prepared by a variety of methods familiar to those skilled in the art. One route described in W. H. Moos et al., *J. Org. Chem.*, 46: 5064-5074 (1981) is illustrated in Scheme 1. A substituted benzaldehyde 1 is treated with trimethyl or triethyl phosphonoacetate 2 in the presence of a base such as 1,8-diazobicyclo[5.4.0]undec-7-ene (DBU) to provide the aryl enoate 3. Conjugate addition of ethyl or methyl cyanoacetate 4 to enoate 3 in the presence of sodium methoxide provides 5 as a mixture of stereoisomers at each chiral center. Reduction of the nitrile of 5 using catalytic hydrogenation with, for example, hydrogen gas and a platinum (IV) oxide catalyst, gives compound 6 as predominantly the trans isomer. Protection of lactam 6 with 4-methoxybenzyl chloride (PMBCl) provides the corresponding N-protected lactam. Subsequent hydrolysis of the methyl ester with, for example, lithium hydroxide then provides acid 7 where P=PMB. Acid 7 may then be subjected to Curtius rearrangement following literature conditions (D. A. Evans, et al *J. Org. Chem.*, 64: 6411-6417 (1999)) to give the corresponding carboxybenzyl carbamate, which is deprotected under hydrogenation conditions in the presence of di-tert-butyl dicarbonate to provide intermediate 8. Deprotection of the lactam of 8 using an oxidant such as cerium ammonium nitrate (CAN) in a solvent such as acetonitrile and water provides IIa.

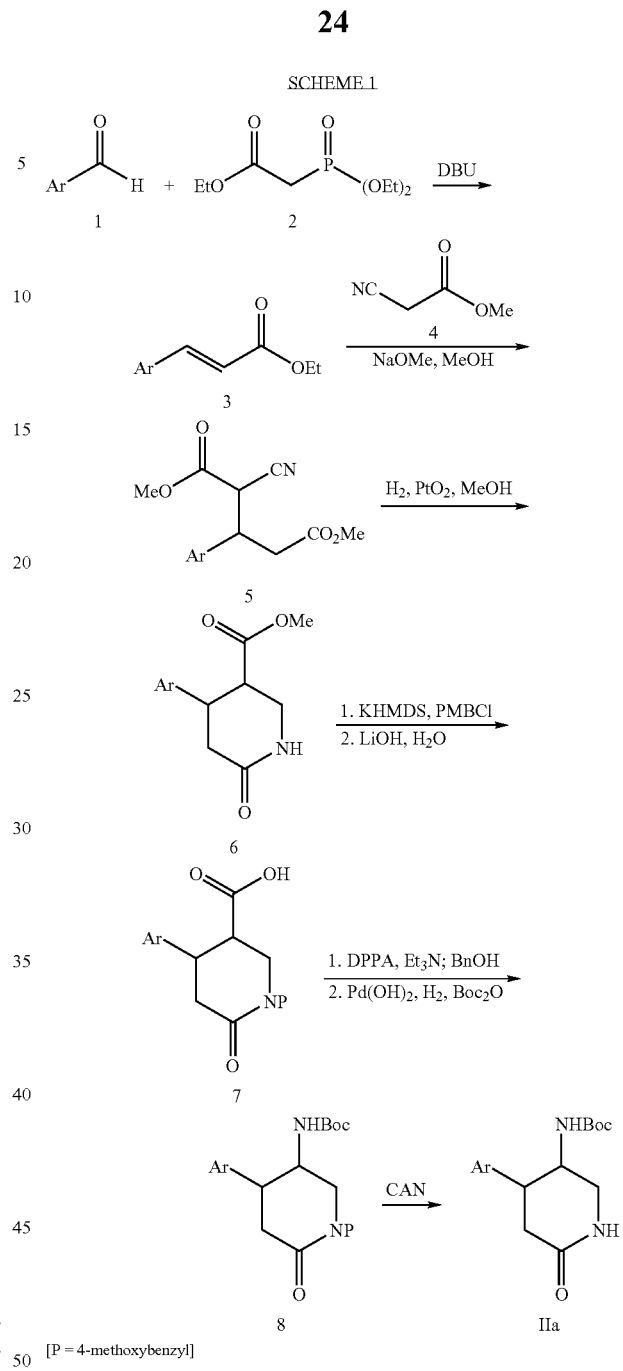

[P = 4-methoxybenzyl]

Compounds of formula I may be prepared as illustrated in Scheme 2 from intermediate IIa described above and intermediate IIIa, wherein U is Cl, Br, I, or triflate. Intermediates IIIa are either commercially available or known in the literature. Intermediates 9 may be prepared by heating IIIa and ma together in the presence of a copper salt such as copper (I) iodide and N,N'-dimethylethylenediamine in the presence of a base such as potassium carbonate or potassium phosphate in solvents such as toluene or ethylene glycol dimethyl ether (DME) according to procedures outlined in A. Klapars, et. al. *J. Am. Chem. Soc.* 124: 7421-7428 (2002) and references contained therein. The protecting group of 9 is then removed with, for example, trifluoroacetic acid or methanolic hydrogen chloride in the case of Boc to give the desired amine I wherein m is 0. The product is purified, if necessary, by crystallization, trituration, preparative thin layer chromatography, flash chromatography on silica gel, such as with a Biotage® apparatus, or HPLC. Compounds that are purified by reverse phase HPLC may be isolated as the corresponding salt. Purification of intermediates is achieved in the same manner.

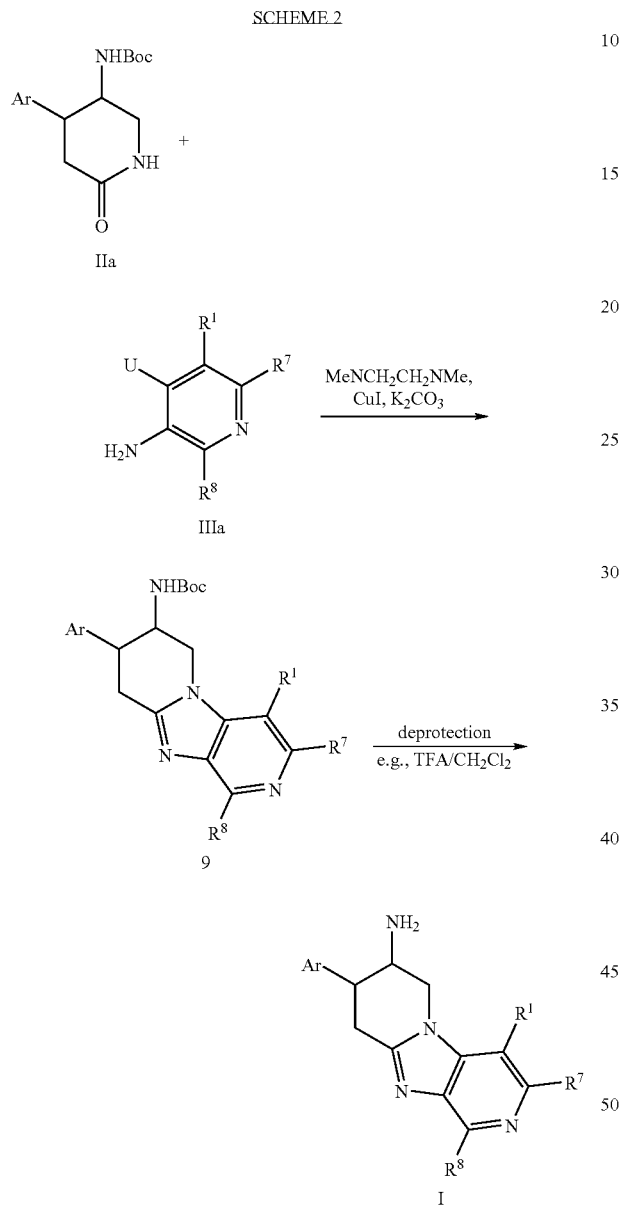

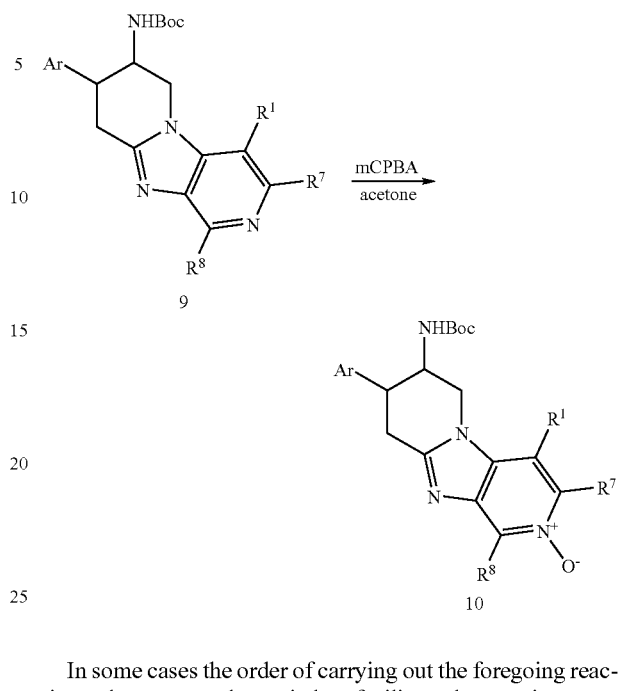

In some cases the product I or synthetic intermediates illustrated in the above schemes may be further modified, for example, by manipulation of substituents on Ar, $R^1$, $R^7$, or $R^8$. These manipulations may include, but are not limited to, reduction, oxidation, alkylation, arylation, acylation, and hydrolysis reactions that are commonly known to those skilled in the art. One such example is illustrated in Scheme 3. Intermediate 9 may be treated with an oxidizing agent such as m-chloroperbenzoic acid in a solvent such as acetone to give the corresponding N-oxide 10. Deprotection as described for Scheme 2 provides the desired amine I wherein m is 1.

In some cases the order of carrying out the foregoing reaction schemes may be varied to facilitate the reaction or to avoid unwanted reaction products. The following examples are provided so that the invention may be more fully understood. These examples are illustrative only and should not be construed as limiting the invention in any way.

INTERMEDIATE 1

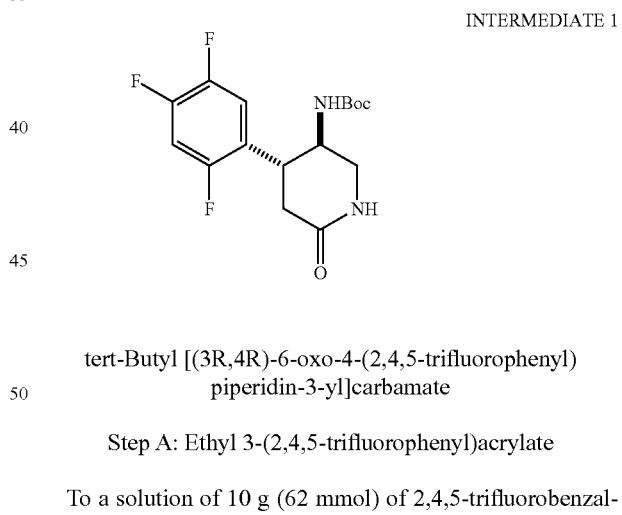

tert-Butyl [(3R,4R)-6-oxo-4-(2,4,5-trifluorophenyl) piperidin-3-yl]carbamate

Step A: Ethyl 3-(2,4,5-trifluorophenyl)acrylate

To a solution of 10 g (62 mmol) of 2,4,5-trifluorobenzaldehyde and 14 mL (70 mmol) of triethyl phosphonoacetate in 200 mL of tetrahydrofuran was added 11 mL (75 mmol) of 1,8-diazobicyclo[5.4.0]undec-7-ene. The solution was stirred at ambient temperature for 4 h, then concentrated in vacuo and dissolved in 800 mL of a 10:1 solution of hexane/ethyl acetate. The resulting solution was washed sequentially with 1N hydrochloric acid, saturated aqueous sodium bicarbonate solution, and saturated aqueous brine (200 mL each). The organic phase was then dried over magnesium sulfate, filtered, and evaporated in vacuo to yield a crude oil. The crude material was then purified by flash chromatography on a Biotage Horizon® system (silica gel, 0 to 15% ethyl acetate/hexanes gradient) to give ethyl 3-(2,4,5-trifluorophenyl)acrylate as a colorless oil. $^1$H NMR (500 MHz, CDCl$_3$): δ 7.71 (d, J=16.2 Hz, 1 H), 7.37 (ddd, J=17.1, 8.7, 1.8 Hz, 1 H), 7.00 (ddd, J=16.2, 9.8, 2.4 Hz, 1 H), 6.46 (d, J=16.2 Hz, 1 H), 4.30 (q, J=7.1 Hz, 2 H), 1.36 (t, J=7.1 Hz, 3 H).

Step B: Dimethyl
2-cyano-3-(2,4,5-trifluorophenyl)pentanedioate

To a solution of 15 mL (64 mmol, 25% in methanol) of sodium methoxide in 200 mL of methanol was added 5.5 mL (62 mmol) of methyl cyanoacetate and the mixture was stirred at ambient temperature for 30 min. To this solution was added 14 g (62 mmol) of the product of step A in 50 mL of methanol and the resulting yellow mixture was heated to reflux for 6 h. The mixture was then quenched carefully at ambient temperature with 1N aqueous hydrochloric acid (100 mL) and concentrated to remove methanol. The resulting mixture was extracted with three 300-mL portions of ethyl acetate, and the organic phases combined and washed sequentially with 1N hydrochloric acid, saturated aqueous sodium bicarbonate solution, and saturated aqueous brine (100 mL each). The organic phase was then dried over magnesium sulfate, filtered, and evaporated in vacuo to yield a viscous oil. The crude material was purified by flash chromatography on a Biotage Horizon® system (silica gel, 0 to 25% ethyl acetate/hexanes gradient) to give the title compound as a mixture of stereoisomers.
$^1$H NMR (500 MHz, CDCl$_3$): δ 7.33-6.96 (m, 2 H), 4.23-3.93 (series of m, 2 H), 3.81-3.67 (series of s, 6 H), 3.05-2.84 (m, 2 H).

Step C: Methyl trans-6-oxo-4-(2,4,5-trifluorophenyl)piperidine-3-carboxylate

To a solution of 26.4 g (83.8 mmol) of dimethyl 2-cyano-3-(2,4,5-trifluorophenyl)pentanedioate from Step B in 120 mL of methanol was added 5.0 g (22 mmol) of platinum(IV) oxide. The reaction mixture was shaken under 50 psi of hydrogen for 16 h at which point the reaction was diluted with 400 mL of a 3:1 mixture of chloroform and 2-propanol to dissolve the desired white solid, and filtered through a pad of Celite. The filter cake was successively washed with three portions of 400 mL of the above solvent mixture. The combined filtrate and washings were concentrated and then taken up in 150 mL of ethyl acetate, stirred for 5 min, then 150 mL of hexanes was added and stirred for 5 min. The white precipitate was filtered to afford the title compound which was used without further purification. LC/MS 288.3 (M+1).

Step D: Methyl trans-1-(4-methoxybenzyl-6-oxo-4-(2,4,5-trifluorophenyl)piperidine-3-carboxylate To a solution of 23.8 g (82.9 mmol) of the product from Step C in 400 mL of a 3:1 mixture of tetrahydrofuran and N,N-dimethylformamide at −78° C. was added 182.3 mL (91.15 mmol) of potassium bis(trimethylsilyl)amide over 0.5 h. The reaction mixture was stirred for 1 h, at which point 16.9 mL (124 mmol) of 4-methoxybenzyl chloride was slowly added over 10 min followed by 0.2 g (0.54 mmol) of tetrabutylammonium iodide. The reaction mixture was stirred for 10 min then warmed to ambient temperature and stirred for 20 h. The mixture was then poured into 400 mL of a 1:1 mixture of saturated aqueous ammonium chloride solution and ethyl acetate. The layers were separated and the aqueous layer extracted with three 150-mL portions of ethyl acetate. The combined organic layers were washed sequentially with 150 mL of water followed by 150 mL of brine. The organic layer was dried over anhydrous magnesium sulfate, filtered, and evaporated in vacuo to yield a viscous oil that was used without further purification. LC/MS 408.2 (M+1).

Step E: trans-1-(4-Methoxybenzyl)-6-oxo-4-(2,4,5-trifluorophenyl)piperidine-3-carboxylic acid To a solution of 33.7 g (82.9 mmol) of the crude product from Step D in 1 L of 3:1 tetrahydrofuran/methanol was added 250 mL (250 mmol) of a 1N aqueous lithium hydroxide solution and the resulting mixture was stirred at ambient temperature for 18 h. The solution was concentrated to 1/3 its volume and slowly acidified with 300 mL of 1N aqueous hydrochloric acid. The resulting white solid was filtered, washed with 50 mL of water followed by 50 mL of methanol and the residual solvent evaporated in vacuo to yield the title acid as a white solid that was used without further purification.
LC/MS 394.1 (M+1).

Step F: Benzyl [trans-1-(4-methoxybenzyl)-6-oxo-4-(2,4,5-trifluorophenyl)piperidin-3-yl]carbamate To 26.3 g (66.8 mmol) of the product of Step E in 500 mL of toluene was added 12.2 nm (86.9 mmol) of triethylamine followed by 18.8 mL (86.9 mmol) of diphenylphosphoryl azide. The slurry was slowly heated to 50° C. over 30 min then to 70° C. over 20 min and held at this temperature for an additional 20 min. The clear brown solution was then heated to reflux over a period of 40 min and stirred at this temperature for an additional 3 h. The reaction mixture was cooled to ambient temperature, 20.8 mL (200.5 mmol) of benzyl alcohol was added, and the reaction mixture was heated to reflux for 3 h. The reaction was cooled to 100° C., stirred for an additional 14 h, then cooled to ambient temperature, and concentrated. The residue was stirred for 5 min in 100 mL of ethyl acetate and filtered to provide the first crop of the title compound. The filtrate was poured into a mixture of 1N aqueous hydrochloric acid (500 mL) and ethyl acetate (250 mL). The resulting mixture was extracted with three 150-mL portions of ethyl acetate, the organic phases combined and washed sequentially with 1N hydrochloric acid, saturated aqueous sodium bicarbonate solution, and saturated aqueous brine (100 mL each). The organic phase was then dried over magnesium sulfate, filtered, and evaporated in vacuo to yield a viscous crude oil. The remaining crude material was purified by flash chromatography on a Biotage Horizon® system (silica gel, 0 to 80% ethyl acetate/hexanes gradient) to give the title compound as a white crystalline solid. LC/MS 499.0 (M+1).

Step G: tert-Butyl[(3R,4R)-1-(4-methoxybenzyl)-6-oxo-4-(2,4,5-trifluorophenyl)piperidin-3-yl]carbamate To 22.4 g (45 mmol) of the product from Step F in 600 mL of methanol was added 12.2 g (56 mmol) of di-tert-butyl dicarbonate and the solution was shaken with 3.3 g of palladium hydroxide (20% on carbon) under 1 atm of hydrogen for 12 h. The mixture was filtered through a pad of Celite and the filter cake washed with 3:1 dichloromethane/methanol and concentrated. The solid was taken up in 1 L of a 1:1 mixture of ethyl acetate and saturated aqueous sodium bicarbonate. The layers were separated and the aqueous layer extracted with four 200-mL portions of ethyl acetate, dried over anhydrous magnesium sulfate, filtered and evaporated in vacuo. The solid was recrystallized from ethyl acetate/hexane to give the title compound and its enantiomer as a white crystalline solid. Chiral HPLC separation (ChiralCel AD-H column, 30% methanol/carbon dioxide) gave the (−)-3S,4S enantiomer B as the more mobile eluting compound and the (+)-3R,4R enantiomer A, as the less mobile eluting compound.

Step H: tert-Butyl [(3R,4R)-6-oxo-4-(2,4,5-trifluorophenyl)piperidin-3-yl]carbamate To 6.7 g (14.4 mmol) of the above (+)-3R,4R enantiomer in 230 mL of acetonitrile at ambient temperature was added 24 g (43.4 mmol) of cerium (IV) ammonium nitrate (CAN) as a solution in 77 mL of water over 10 min, and the reaction mixture was stirred for 1.5 h. The reaction mixture was then quenched with saturated sodium bisulfite and stirred for 5 min. The solid was filtered through a Celite pad and washed with 100 mL of acetonitrile and the combined filtrate concentrated. The crude residue was dissolved in 200 mL of a 1:1 mixture of ethyl acetate and brine, the layers were separated and the aqueous layer extracted with five 50-mL portions of ethyl acetate. The combined organic layers were dried over magnesium sulfate, filtered, and evaporated in vacuo to yield a yellow solid. The crude material was then purified by flash chromatography on a Biotage Horizon® system (silica gel, 0 to 100% ethyl acetate/hexanes gradient followed by 0 to 20% methanol/ethyl acetate) to give the title compound as a pale yellow solid. LC/MS 345.2 (M+1).

INTERMEDIATE 2

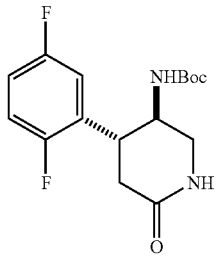

tert-Butyl [(3R,4R)-6-oxo-4-(2,5-difluorophenyl)piperidin-3yl]carbamate tert-Butyl [(3R,4R)-6-oxo-4-(2,5-difluorophenyl)piperidin-3-yl]carbamate was made from 2,5-difluorobenzaldehyde by following essentially the procedure described for Intermediate 1.

Example 1

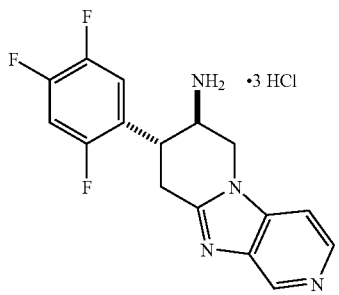

(7R,8R)-8-(2,4,5-Trifluorophenyl)-6,7,8,9-tetrahydropyrido[3',4'4,5]imidazo[1,2-a]pyridin-7-amine trihydrochloride Step A: 2,2-Dimethyl-N-pridin-3-ylpropanamide To a solution containing 50 g (531 mmol) of 3-aminopyridine and 139 mL (797 mmol) of N,N-diisopropylethylamine in 800 mL of dichloromethane at 0° C. was carefully added through an addition funnel 72 mL (584 mmol) of pivaloyl chloride. The reaction mixture was stirred at 0° C. for 30 min then concentrated in vacuo. To the residue was added 600 mL of ethyl acetate and the organic solution was washed sequentially with water, 0.5N aqueous sodium bicarbonate solution and saturated aqueous brine (300 mL each). The organic layer was dried over anhydrous sodium sulfate, filtered and evaporated in vacuo. To the crude solid was added 150 mL of ethyl acetate. The mixture was stirred vigourously for 30 min, then 300 mL of hexane was added and the mixture was stirred for an additional 30 min. The resultant crystalline solid was filtered and washed with 400 mL of 10% ethyl acetate/hexane to give the title compound. $^1$H NMR (500 MHz, CDCl$_3$): δ 8.57 (d, J=2.5 Hz, 1H), 8.36 (dd, J=4.8, 1.4 Hz, 1H), 8.21-8.19 (m, 1H), 7.47 (br s, 1H), 7.30-7.27 (m, 1H), 1.36 (s, 9H).

Step B: N-(4-Bromopyridin-3-yl)-2,2-dimethylpropanamide

To a solution containing 25 g (140 mmol) of the product from Step A and 52.2 mL (350 mmol) of redistilled N,N,N',N'-tetramethylethylenediamine in 350 mL of dry THF under nitrogen at −78° C. was slowly added via cannula 140 mL (350 mmol) of n-butyllithium (2.5N in hexane). The reaction mixture was stirred at −78° C. for 30 min then at −10° C. for 90 min. The reaction mixture was then cooled to −78° C. and 30.2 mL (350 mmol) of 1,2-dibromoethane was slowly added. The mixture was stirred at −78° C. for 30 min, at −10° C. for 90 min then quenched with saturated aqueous ammonium chloride solution. A 600 mL portion of ethyl acetate was next added and the mixture was washed sequentially with water and saturated aqueous brine (400 mL each). The organic layer was dried over anhydrous sodium sulfate, filtered and evaporated in vacuo. The crude material was purified by flash chromatography on a Biotage Horizon® system (silica gel, 0 to 100% ethyl acetate/hexanes gradient) to give the title compound. $^1$H NMR (500 MHz, CDCl$_3$): δ 9.54 (s, 1H), 8.18 (d, J=5.2 Hz, 1H), 7.86 (br s, 1H), 7.51 (d, J=5.3 Hz, 1H), 1.39 (s, 9H).

Step C: 3-Amino-4-bromopyridine

To a solution containing 15.7 g (61 mmol) of the product from Step B in 100 mL of 2-propanol was added 50 mL of 3N aqueous potassium hydroxide solution. The reaction mixture was heated to reflux for 5 h then cooled to ambient temperature and extracted with three portions of ethyl ether (100 mL each). The combined organic extracts were washed with brine, dried over anhydrous sodium sulfate, filtered and evaporated in vacuo. The crude material was purified by flash chromatography on a Biotage Horizon® system (silica gel, 0 to 100% ethyl acetate/hexanes gradient) to give the title compound as a viscous oil which solidified upon standing. $^1$H NMR (500 MHz, CDCl$_3$): δ 8.10 (s, 1H), 7.80 (d, J=5.3 Hz, 1H), 7.34 (d, J=5.3 Hz, 1H), 4.19 (br s, 2H).

Step D: tert-Butyl {(7R,8R)-8-(2,4,5-trifluorophenyl)-6,7,8,9-tetrahydropyrido[3',4'4,5]imidazo[1,2-a]pyridin-7-yl}carbamate To an oven-dried flask charged with 2.8 g (8.13 mmol) of Intermediate 1, 1.97 g (11.4 mmol) of the product from Step C, 136 mg (0.72 mmol) of copper(I) iodide, 1.97 g (14.2 mmol) of potassium carbonate, and 20 mL of dry toluene was added 0.153 mL (1.42 mmol) of N,N'-dimethylethylenediamine and the mixture was heated to reflux for 24 h. Another portion of copper(I) iodide (136 mg, 0.72 mmol) and N,N'-dimethylethylenediamine (0.153 mL, 1.42 mmol) was added and the reaction mixture was heated to reflux for an extra 16 h. The mixture was cooled to ambient temperature, filtered through a Celite pad and the filter cake rinsed with 300 mL of ethyl acetate. The ethyl acetate solution was washed with 100 mL of a 1:1 mixture of saturated sodium bicarbonate solution and saturated aqueous brine. The layers were separated and the aqueous layer extracted with four 100-mL portions of ethyl acetate. The combined organic phases were dried over anhydrous magnesium sulfate, filtered and evaporated in vacuo. The residue was purified by flash chromatography on a Biotage Horizon® system (silica gel, 12 to 100% ethyl acetate/hexanes gradient then 0 to 20% methanol/ethyl acetate gradient) to give the title compound. $^1$H NMR (500 MHz, CD$_3$OD): δ 8.84 (s, 1H), 8.35 (d, J=5.7 Hz, 1H), 7.62 (d, J=5.7 Hz, 1H), 7.45 (ddd, J=15.6, 9.7, 2.3 Hz, 1H), 7.22 (ddd, J=16.9, 6.9, 3.4 Hz, 1H), 4.63-4.57 (m, 2H), 4.00-3.95 (m, 1H), 3.72 (dd, J=17.8, 9.6 Hz, 1H), 3.45-3.43 (m, 2H), 1.33 (s, 9H). LC/MS 419.11 (M+H).

Step E: (7R,8R)-8-(2,4,5-Trifluorophenyl)-6,7,8,9-tetrahydropyrido[3',4':4,5]imidazo[1,2-a]pyridin-7-amine trihydrochloride To a solution containing 3.8 g (9.1 mmol) of product from Step D in 60 mL of ethyl acetate, at 0° C., 150 mL of saturated hydrogen chloride in ethyl acetate was added. The reaction mixture was stirred at 0° C. for 30 min then at ambient temperature for 60 min. The white precipitate was filtered, rinsed with 30 mL of a 1:1 mixture of ethanol/ethyl acetate then with 100 mL of ethyl ether. The product was then dried under high vacuum for 12 h to yield the title compound as a white solid. $^1$H NMR (500 MHz, CD$_3$OD): δ 9.28 (s, 1H), 8.66 (d, J=6.6 Hz, 1H), 8.31 (d, J=6.6 Hz, 1H), 7.59 (ddd, J=17.6, 8.5, 1.8 Hz, 1H), 7.38 (ddd, J=17.0, 10.3, 6.7 Hz, 1H), 5.06 (ddd, J=10.5, 3.5 Hz, 1H), 4.53-4.44 (m, 2H), 4.01 (ddd, J=16.0, 10.5, 5.7 Hz, 1H), 3.71-3.59 (m, 2H). LC/MS 319.2 (M+H).

Following essentially the procedures outlined for Example 1, the Examples listed in Table 1 were prepared.

TABLE 1

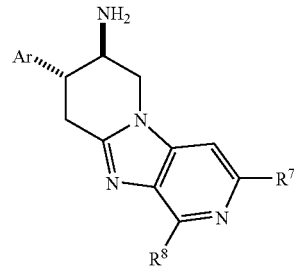

| Example | Ar | R$^7$ | R$^8$ | Mass spectrum (M + 1) |
|---|---|---|---|---|
| 2 | 2,4,5-trifluorophenyl | H | Cl | 353.4 |
| 3 | 2,4,5-trifluorophenyl | CF$_3$ | H | 387.0 |

TABLE 1-continued

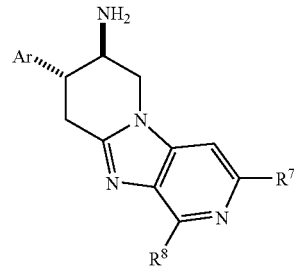

| Example | Ar | R$^7$ | R$^8$ | Mass spectrum (M + 1) |
|---|---|---|---|---|
| 4 | 2,4,5-trifluorophenyl | F | H | 337.1 |
| 5 | 2,4,5-trifluorophenyl | Cl | H | 353.1 |
| 6 | 2,5-difluorophenyl | H | H | 301.2 |
| 7 | 2,5-difluorophenyl | F | H | 319.2 |
| 8 | 2,5-difluorophenyl | CF$_3$ | H | 369.1 |

Example 9

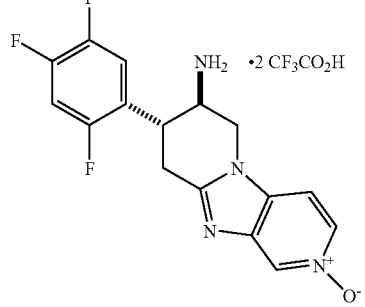

(7R,8R)-S-(2,4,5-Trifluorophenyl)-6,7,8,9-tetrahydropyrido[3',4':4,5]imidazo[1,2-a]pyridin-7-amine 2-oxide bis trifluoroacetic acid salt To a solution of the intermediate from Step D of Example 1 in acetone (2 mL) was added m-chloroperbenzoic acid (31 mg). After stirring for 90 min, the reaction mixture was concentrated and the residue dissolved in ethyl acetate (15 mL), sequentially washed with saturated aqueous sodium bicarbonate solution (5 mL) and brine (5 mL), dried over anhydrous sodium sulfate, filtered and concentrated. The crude residue was dissolved in 4 mL of 1:1 dichloromethane/trifluoroacetic acid and stirred at ambient temperature for 60 min. The solution was concentrated in vacuo and the crude oil was purified by reverse phase HPLC (YMC Pro-C18 column, gradient elution 0 to 75% acetonitrile/water with 0.1% TFA) to afford the title compound as a colorless solid. LC-MS 335.2 (M+1).

Example 10

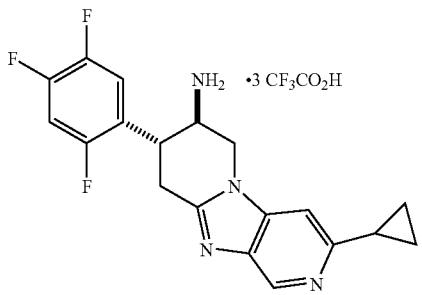

(7R,8R)-3-Cyclopropyl-8-(2,4,5-trifluorophenyl)-6,7,8,9-tetrahydropyrido[3',4':4,5]imidazo[1,2-a]pyridine-7-amine tris trifluoroacetic acid salt Step A: tert-Butyl [(7R,8R)-3-cyclopropyl-8-(2,4,5-trifluorophenyl)-6,7,8,9-tetrahydropyrido[3',4':4,5]imidazo[1,2-a]pyridine-7-yl]carbamate An oven dried flask charged with 52 mg (0.115 mmol) of tert-butyl [(7R,8R)-3-chloro-8-(2,4,5-trifluorophenyl)-6,7,8,9-tetrahydropyrido[3',4':4,5]imidazo[1,2-a]pyridine-7-yl]carbamate (Boc-protected intermediate of Example 5), 12 mg (0.14 mmol) of cyclopropylboronic acid, 64 mg (0.46 mmol) of potassium carbonate, 13 mg (0.0115 mmol) of tetrakis(triphenylphosphine)palladium(0) and 1.5 mL of dry dioxane was put under nitrogen and heated to reflux for 72 h. The reaction mixture was cooled to ambient temperature, filtered through a pad of Celite and the filter cake rinsed with 50 mL of ethyl acetate. The filtrate was evaporated in vacuo and the crude residue was purified directly by reverse phase HPLC (YMC Pro-C18 column, gradient elution, 5% to 90% acetonitrile/water with 0.1% TFA) to afford the title compound as a white foam. LC/MS 459.2 (M+1).

Step B: (7R,8R)-3-Cyclopropyl-8-(2,4,5-trifluorophenyl)-6,7,8,9-tetrahydropyrido[3',4 4,5]imidazo[1,2-a]pyridine-7-amine tris trifluoroacetic acid salt To the product from Step A was added 4 mL of 1:1 methylene chloride/trifluoroacetic acid and the solution was stirred for 30 min then concentrated in vacuo. The residue was purified by reverse phase HPLC (YMC Pro-C18 column, gradient elution, 0% to 65% acetonitrile/water with 0.1% TFA) to afford the title compound as a white foam. LC/MS 359.2 (M+1).

Example 11

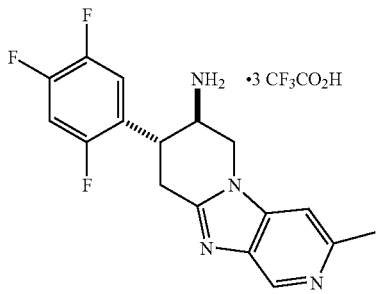

(7R,8R)-3-Methyl-8-(2,4,5-trifluorophenyl)-6,7,8,9-tetrahydropyrido[3',4':4,5]imidazo[1,2-a]pyridine-7-amine tris trifluoroacetic acid salt Following essentially the procedures outlined for Example 10 but using methylboronic acid in place of cyclopropylboronic acid, Example 11 was prepared. LC/MS 333.17 (M+1).

Example 12

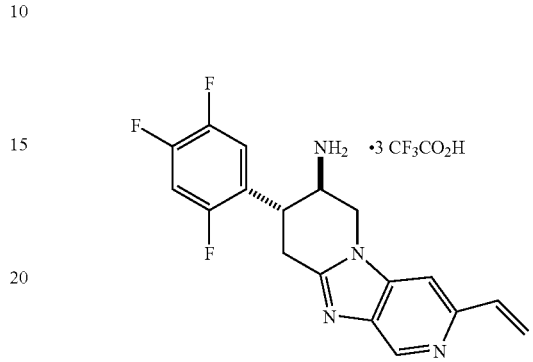

(7R,8R)-8-(2,4,5-Trifluorophenyl)-3-vinyl-6,7,8,9-tetrahydropyrido[3',4':4,5]imidazo[1,2-a]pyridine-7-amine tris trifluoroacetic acid salt Step A: tert-Butyl [(7R,8R)-8-(2,4,5-trifluorophenyl)-3-vinyl-6,7,8,9-tetrahydropyrido[3',4':4,5]imidazo[1,2-a]pyridine-7-yl]carbamate An oven dried flask charged with 30 mg (0.066 mmol) of tert-butyl [(7R,8R)-3-chloro-8-(2,4,5-trifluorophenyl)-6,7,8,9-tetrahydropyrido[3',4':4,5]imidazo[1,2-a]pyridine-7-yl]carbamate, 0.024 mL (0.079 mmol) of tributyl(vinyl)tin, 23 mg (0.020 mmol) of tetrakis(triphenylphosphine)palladium (0) and 1.5 mL of dry dioxane was put under nitrogen and heated to reflux for 72 h. The reaction mixture was cooled to ambient temperature, filtered through a pad of Celite and the filter cake rinsed with 50 mL of ethyl acetate. The filtrate was evaporated in vacuo and the crude residue was purified directly by reverse phase HPLC (YMC Pro-C18 column, gradient elution, 5% to 90% acetonitrile/water with 0.1% TFA) to afford the title compound as a white foam. LC/MS 445.2 (M+1).

Step B: (7R,8R)-8-(2,4,5-Trifluorophenyl)-3-vinyl-6,7,8,9-tetrahydropyrido[3',4':4,5]imidazo[1,2-a]pyridine-7-amine tris trifluoroacetic acid salt To the product from Step A was added 2.0 mL of methylene chloride and 2.0 mL of trifluoroacetic acid, and the solution was stirred for 30 min then concentrated in vacuo. The residue was purified by reverse phase HPLC (YMC Pro-C18 column, gradient elution, 0% to 65% acetonitrile/water with 0.1% TFA) to afford the title compound as a white foam. LC/MS 345.2 (M+1).

Example of a Pharmaceutical Formulation

As a specific embodiment of an oral pharmaceutical composition, a 100 mg potency tablet is composed of 100 mg of any of Examples 1-12, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

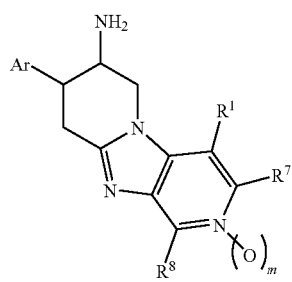

(I)

or a pharmaceutically acceptable salt thereof; wherein
m is 0 or 1;
each n is independently 0, 1, or 2;
Ar is phenyl unsubstituted or substituted with one to five $R^2$ substituents;
each $R^2$ is independently selected from the group consisting of fluorine, chlorine, methyl, and trifluoromethyl;
$R^1$, $R^7$ and $R^8$ are each independently selected from the group consisting of
  hydrogen,
  hydroxy,
  halogen,
  $C_{1-10}$ alkoxy, wherein alkoxy is unsubstituted or substituted with one to five substituents independently selected from halogen or hydroxy,
  $C_{1-10}$ alkyl, wherein alkyl is unsubstituted or substituted with one to five substituents independently selected from halogen or hydroxy,
  $C_{1-10}$ alkenyl, unsubstituted or substituted with one to five substituents independently selected from halogen or hydroxy,
  $(CH_2)_n$—$C_{3-6}$ cycloalkyl, wherein cycloalkyl is unsubstituted or substituted with one to three substituents independently selected from halogen, hydroxy, cyano, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
wherein any individual methylene ($CH_2$) carbon atom in $(CH_2)_n$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
$R^3$ and $R^4$ are each independently selected from the group consisting of
  hydrogen,
  $(CH_2)_n$-phenyl,
  $(CH_2)_n$—$C_{3-6}$ cycloalkyl, and
  $C_{1-6}$ alkyl,
wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens;
each $R^5$ is independently $C_{1-6}$ alkyl, wherein alkyl is unsubstituted or substituted with one to five substituents independently selected from halogen and hydroxy; and
$R^6$ is hydrogen or $R^5$.

2. The compound of claim 1 wherein m is 0.
3. The compound of claim 1 wherein m is 1.
4. The compound of claim 1 wherein Ar is 2,4,5-trifluorophenyl or 2,5-difluorophenyl.
5. The compound of claim 1 wherein $R^1$, $R^7$ and $R^8$ are each independently selected from the group consisting of
  hydrogen,
  halogen,
  $C_{1-4}$ alkoxy, wherein alkoxy is unsubstituted or substituted with one to five fluorines,
  $C_{1-4}$ alkyl, wherein alkyl is unsubstituted or substituted with one to five fluorines,
  $C_{1-4}$ alkenyl, unsubstituted or substituted with one to five fluorines, and
  $C_{3-6}$ cycloalkyl.
6. The compound of claim 5 wherein $R^1$ is hydrogen.
7. The compound of claim 1 of structural formula Ia or Ib having the indicated stereochemical configuration at the two stereogenic carbon atoms marked with an *:

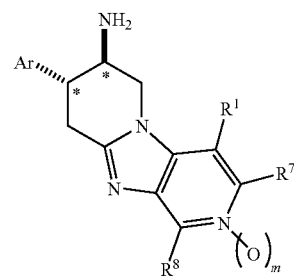

(Ia)

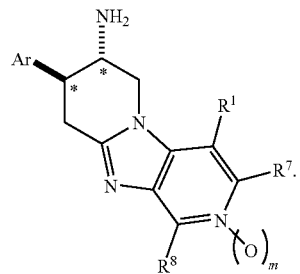

(Ib)

8. The compound of claim 7 of structural formula Ia having the indicated absolute stereochemical configuration at the two stereogenic carbon atoms marked with an *:

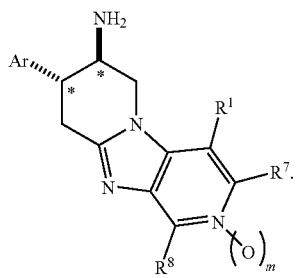

(Ia)

9. The compound of claim 8 wherein m is 0; $R^1$ is hydrogen; Ar is 2,4,5-trifluorophenyl or difluorophenyl; and $R^7$ and $R^8$ are each independently selected from the group consisting of hydrogen, halogen, $C_{1-4}$ alkoxy, wherein alkoxy is unsubstituted or substituted with one to five fluorines, $C_{1-4}$ alkyl, wherein alkyl is unsubstituted or substituted with one to five fluorines, $C_{1-4}$ alkenyl, unsubstituted or substituted with one to five fluorines, and $C_{3-6}$ cycloalkyl.

10. The compound of claim 8 wherein m is 1; $R^1$ is hydrogen; Ar is 2,4,5-trifluorophenyl or difluorophenyl; and $R^7$ and $R^8$ are each independently selected from the group consisting of hydrogen, halogen, $C_{1-4}$ alkoxy, wherein alkoxy is unsubstituted or substituted with one to five fluorines, $C_{1-4}$ alkyl, wherein alkyl is unsubstituted or substituted with one to five fluorines, $C_{1-4}$ alkenyl, wherein alkenyl is unsubstituted or substituted with one to five fluorines, and $C_{3-6}$ cycloalkyl.

11. The compound of claim 8 which is selected from the group consisting of:

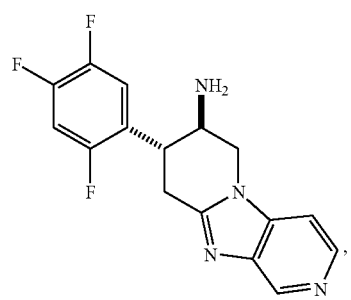

,

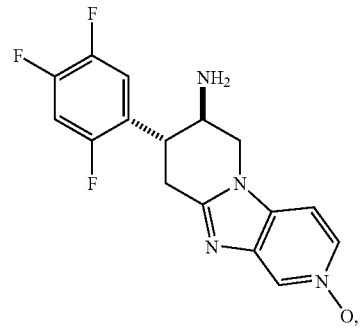

,

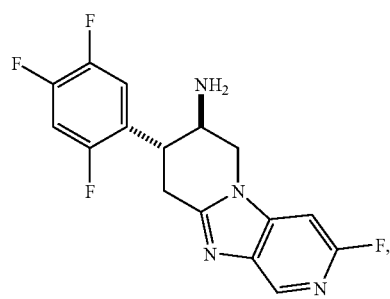

,

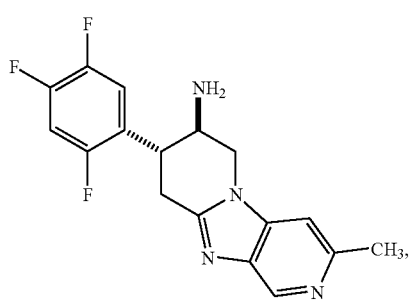

,

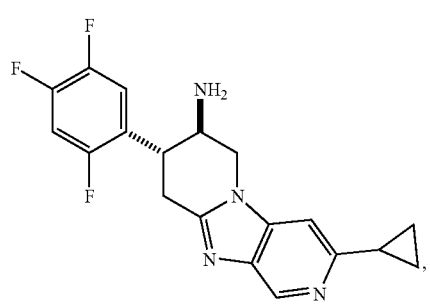

,

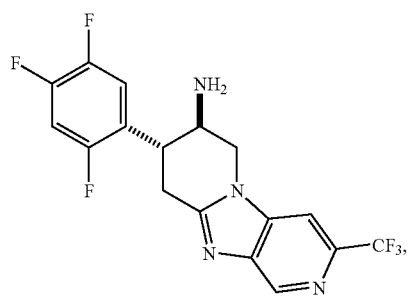

,

-continued

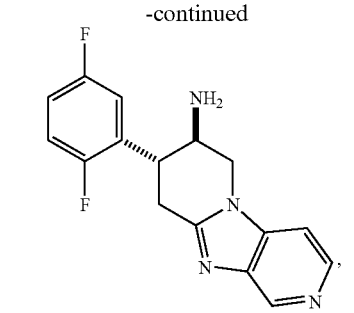

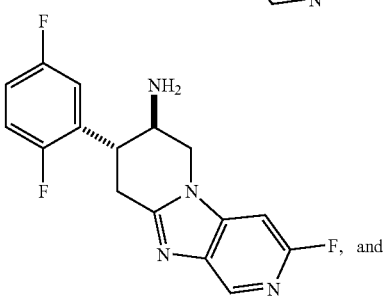

F, and

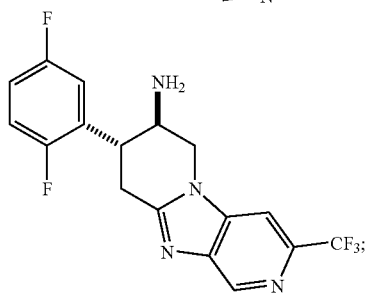

or a pharmaceutically acceptable salt thereof.

12. The compound of claim 11 which is

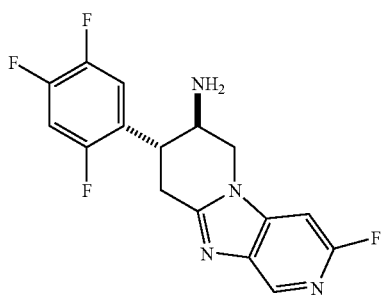

or a pharmaceutically acceptable salt thereof.

13. The compound of claim 11 which is

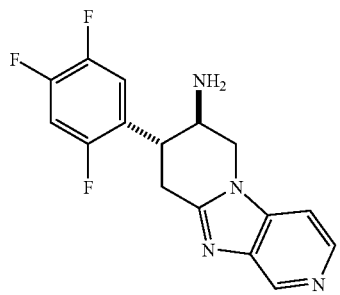

or a pharmaceutically acceptable salt thereof.

14. The compound of claim 11 which is

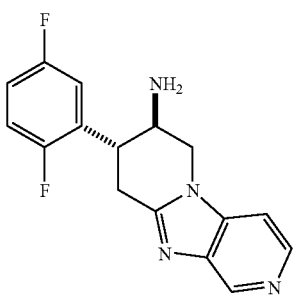

or a pharmaceutically acceptable salt thereof.

15. A pharmaceutical composition which comprises a compound of claim 1 and a pharmaceutically acceptable carrier.

16. The pharmaceutical composition of claim 15 additionally comprising metformin.

17. A method of treating Type 2 diabetes comprising administering a therapeutically effective amount of a compound of claim 1 to a patient in need thereof.

* * * * *

UNITED STATES PATENT AND TRADEMARK OFFICE
CERTIFICATE OF CORRECTION

PATENT NO. : 8,017,624 B2
APPLICATION NO. : 11/990037
DATED : September 13, 2011
INVENTOR(S) : Jason M. Cox, Scott D. Edmondson and Anthony Mastracchio Page 1 of 1

It is certified that error appears in the above-identified patent and that said Letters Patent is hereby corrected as shown below:

On the Title page, item 54 and Col. 1, line 1, delete "FUSED AMINOPIPERIDINES AS DIPEPTIDYI PEPTIDASE-IV INHIBITORS FOR THE TREATMENT OR PREVENTION OF DIABETES" should read -- FUSED AMINOPIPERIDINES AS DIPEPTIDYL PEPTIDASE-IV INHIBITORS FOR THE TREATMENT OR PREVENTION OF DIABETES --.

Signed and Sealed this
Fourteenth Day of February, 2012

David J. Kappos
*Director of the United States Patent and Trademark Office*